United States Patent [19]

Bowlin et al.

[11] Patent Number: 4,905,712
[45] Date of Patent: Mar. 6, 1990

[54] HEAD RESTRAINT SYSTEM

[75] Inventors: Colleen M. Bowlin; Jerry T. Bowlin, both of San Antonio, Tex.

[73] Assignee: ErgoMed, Inc., San Antonio, Tex.

[21] Appl. No.: 390,834

[22] Filed: Aug. 8, 1989

[51] Int. Cl.⁴ .................. A61F 13/00; A61G 1/00
[52] U.S. Cl. ........................ 128/870; 5/82 R
[58] Field of Search ............ 128/869, 870, 871, 872, 128/873, 874, 875, 84 R, 84 C, 87 B; 5/440, 441, 442, 444, 445, 82 R; 269/322

[56] References Cited

U.S. PATENT DOCUMENTS

| | | | |
|---|---|---|---|
| 2,033,779 | 3/1936 | Monk | 5/82 |
| 2,276,256 | 3/1942 | Visness | 5/82 |
| 2,351,146 | 6/1944 | Pike | 5/82 |
| 2,361,328 | 10/1944 | Springer | 5/82 |
| 2,489,828 | 11/1949 | Springer | 5/82 R |
| 2,650,373 | 9/1953 | Zeller | 5/82 |
| 2,695,415 | 11/1954 | Holton | 5/440 |
| 3,271,796 | 9/1966 | Dillman | 5/82 R |
| 3,578,383 | 5/1971 | Earl | 297/391 |
| 3,707,734 | 3/1971 | Matthews | 5/82 |
| 3,897,777 | 8/1975 | Morrison | 128/869 |
| 4,034,748 | 10/1975 | Winner | 128/87 R |
| 4,124,908 | 10/1977 | Burns et al. | 5/82 |
| 4,182,322 | 8/1978 | Miller | 128/869 |
| 4,297,994 | 11/1979 | Bashaw | 128/869 |
| 4,571,757 | 7/1984 | Zolecki | 5/82 R |
| 4,723,327 | 2/1988 | Smith | 5/82 R |
| 4,783,862 | 11/1988 | Murphy | 5/82 R |

Primary Examiner—Robert A. Hafer
Assistant Examiner—Michael Brown
Attorney, Agent, or Firm—Bacon & Thomas

[57] ABSTRACT

A head restraint system for use with a backboard includes a stretchable base pad which defines a rectangular envelope for fitting tightly over one end of the backboard and a pair of head blocks which are adapted to engage a patient's head. The base pad is positioned on the backboard and under a patient's head and the pair of head blocks positioned thereon with one on each side of the patient's head. A base portion of each of the blocks includes hook material for attachment to a top surface of the base pad. The base pad also includes at least one ring-like element on one edge thereof and straps are provided for passing through the ring-like element to press and hold the head blocks downwardly against the upper surface of the base pad and inwardly against the patient's head.

9 Claims, 1 Drawing Sheet

HEAD RESTRAINT SYSTEM

BACKGROUND OF THE INVENTION

This invention relates to a head restraint system for use with a spineboard or backboard and more particularly to a head restraint system for use in immobilizing the head of an injured patient during the transportation of the patient from the scene of the accident to a hospital.

In emergency medical situations, it is frequently desirable to move a patient from the scene of an accident to a hospital before the extent of any injuries are known. In many such circumstances, the paramedics or ambulance attendants are required to immobilize a patient by strapping the patient to a backboard and to immobilize the head to avoid possible complications and/or aggravation of the injuries during the transportation of the patient.

The use of backboards and headblocks for immobilizing the head of an injured patient are well known. Such blocks are typically in the shape of a polyhedron or parallelpiped and are held in place on the backboard and against the sides of a patient's head by a strap or straps.

One example of a head restraint system is disclosed in the U.S. Pat. No. 4,124,908, of Burns et al., in which the head blocks are held in place next to a foam pad by means of Velcro strips and a releasable strap member. The head blocks disclosed therein also define a concave surface for engaging the sides of a patient's head. Other similar blocks including an opening therein for viewing the interior of a patient's ears for bleeding and fluid have also been used in connection with backboards.

Nevertheless, there has been a continuing demand for an improved effective head restraint system which is relatively easy to use, easy to adjust and, because of the emergency environment where these systems often become lost, misplaced, dirty or badly soiled, relatively inexpensive. There is also a demand for a head restraint system Which is adaptable for most conventional backboards, spineboards or stretchers, lightweight, compact and Which may be reused or at times discarded after a single use.

Accordingly, Applicants have developed an improved head restraint system to meet the requirements of today's emergency medical service environment as described hereinafter.

SUMMARY OF THE INVENTION

In essence, a head restraint system for use in transporting an injured patient on a longitudinally extending spine or backboard includes a stretchable base pad and a pair of head blocks. The stretchable base pad that preferably defines a rectangular envelope having a top and bottom surface superposed on each other and with at least a portion of each of three sides thereof closed to form a pair of lateral edges and a top edge with the fourth or bottom side open therealong. The envelope is constructed and arranged so that it can be stretched in a lateral direction parallel to its open side and slipped over one end of the spine or backboard and pulled downwardly along the longitudinal axis of the backboard until the top edge engages the end of the backboard and upon release of the lateral stretch the envelope tightly engages the backboard.

Each head block defines a longitudinally and upwardly extending unit having a base portion which is adapted to engage the top layer of the base pad so that the upwardly extending portion thereof is adapted to be pressed against the side of a patient's head. Means such as a Velcro strip are disposed on the base of the block for holding the block onto the top layer of the pad and positioned on each side of the patient's head. Fastening means such as D-shaped rings are also fixed to at least each lateral edge of the base pad, and a strap provided to engage the fastening means or rings. The purpose of the rings and strap are to press the blocks downwardly against the top layer of the pad and also inwardly against the side of the patient's head to thereby prevent movement of the patient's head during any movement of the patient.

DETAILED DESCRIPTION OF A PREFERRED EMBODIMENT

Figure 1:
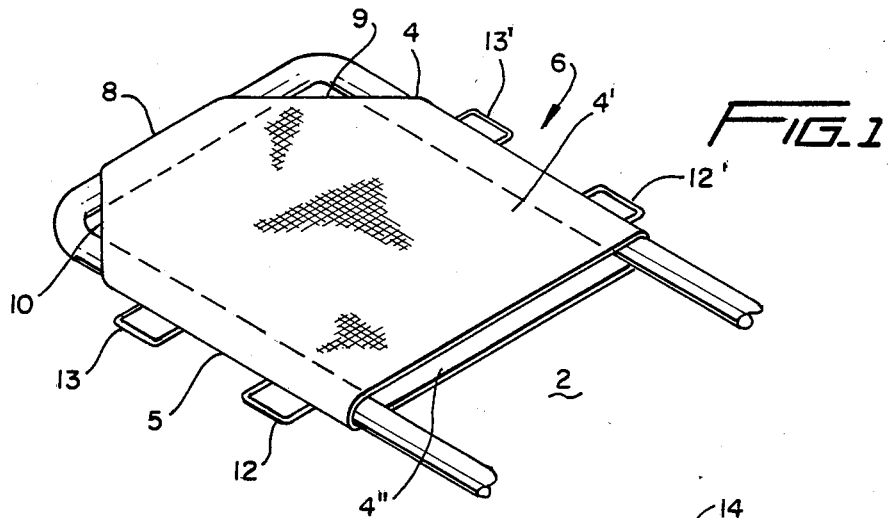
FIG. 1 is a perspective view of a base pad fixed to a backboard in accordance with a first embodiment of the invention.

As illustrated in FIGS. 1–4, a conventional backboard or spineboard 2 hereinafter sometimes referred to as a spine/backboard, has a base pad 4 which is fitted onto one end of the backboard 2. The base pad as shown more clearly in FIG. 1, includes a top and bottom layer 4' 4" which are superposed one above the other but separable when the base pad 4 is installed on one end of the backboard 2. The base pad 2 is at least partially closed on each of three sides. For example, lateral edges 5 and 6 are closed along the lower portion thereof while a top edge s is closed along a portion in the middle thereof to thereby form an envelope with two open corners at 9 and 10. These open corners facilitate the application of the envelope on the backboard by allowing the attendant to see that the top of board 2 is tightly engaging the upper edge 8.

Figure 2:
FIG. 2 is a perspective view of the base pad of FIG. 1 with a pair of head blocks thereon in accordance with the preferred embodiment of the invention.
Figure 3:
FIG. 3 is a perspective view illustrating the base pad and head blocks of FIGS. 1 and 2 fixed to backboard and held thereon by a pair of straps.

A pair of longitudinally and upwardly extending head blocks 14 and 15 shown in FIGS. 2 and 3, each include a base portion 16, 16' and upwardly extending portions 17, 17', defined by converging concave and convex surfaces 18, 18' and 19, 19' respectively which curve upwardly from the bases 16, 16' so that the concave surfaces 18, 18', are adapted to fit against the sides of a patient's head. Each of the head blocks 16 and 16' also define a transverse opening 20, 20' which is approximately parallel to the lateral axis of the backboard 2 and extend therethrough. The openings 20, 20' are provided so that the paramedics, ambulance attendants and/or physician can see the patient's ears and check them for bleeding or fluid discharge. The openings also enable the patient to hear any questions and/or reassurances.

The base pad 10 also has a pair of D-shaped rings 12, 12', 13 and 13' disposed on the lateral edges 5 and 6. The D-shaped rings 12, 12', 13 and 13' protrude outwardly from edges 5 and 6 and are adapted to receive the ends of straps 22 and 23 passed therethrough and therearound for forcing and holding the blocks 14 and 15 downwardly against the layer 4' and inwardly against the sides of a patient's head as illustrated in FIG. 3. Each of the straps 22 and 23 includes fastening means 24 such as a piece of adhesive or preferably a series of hooks, i.e., a velcro fastener on each end thereof for engagement with an inner portion of the straps 22, 23 in the manner shown.

In a preferred embodiment of the invention, the base portion 16 (see FIG. 4) includes two hook-like fasteners 26 and 27, such as Velcro strips along two sides thereof, for engaging the fabric-like upper layer 4' and aid in the positioning or temporary fastening of blocks 14 and 15 against the sides of the patient's head. The hook-like fasteners are disposed on the base portion of the block as opposed to the pad, to avoid the likelihood of a patient's head pressed against the hook-like fastener.

Figure 4:
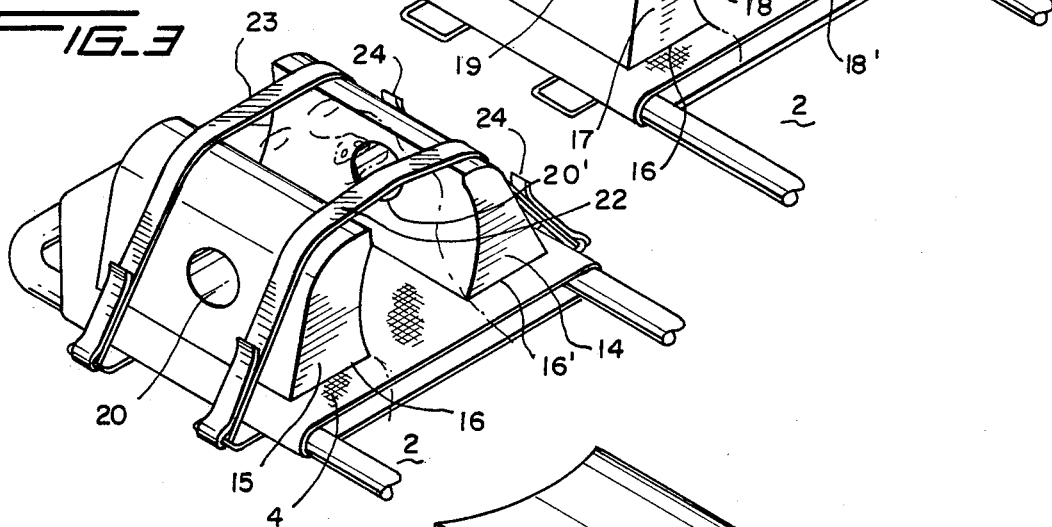
FIG. 4 is a perspective view illustrating a bottom or base portion of a head block according to a second embodiment of the invention.
Figure 4:

FIG. 4 also illustrates a second embodiment of the invention wherein the block 15 includes an internal bladder (not shown) and an inflatable member and valve for inflating the block 15 in the same manner as an inflatable splint. In this embodiment, the materials and valve assembly used in manufacturing the blocks are of conventional design a will be well understood by those skilled in the art of producing inflatable splints.

In the application or use of a head restraint system according to the presently preferred embodiment of the invention, the base pad 4, When laterally stretched, is between 16" and 18" wide and about 16" from the top edge 8 to its bottom edge. The pad 4 is only stretchable in the lateral direction and in a stretched condition slides easily over the top or upper end of backboard 2. Upon release of the lateral stretch, the material contracts and returns to its original state to tightly engage the backboard 2 with its upper edge s snugly against the one end of the backboard 2 and lateral edges 5 and 6 snugly against each side of the backboards. The base pad 4 should fit tightly on the backboard and may be reversed if one side become soiled or appears dirty. However, it is not recommended to turn the envelope inside out because of the ring-structure and also because of the material used in constructing the base pad 4.

In a preferred form, the base pad 4 is made from a polyester urethane foam (polyester resin and polyisocyanate) which is laminated to a style 19029 100% nylon brushed tricot and may be available from San Antonio Foam Fabricators in San Antonio, Tex. In forming the preferred base pad, the foam is heated with a natural gas flame to the point of pyrolysis. The residue is tacky for a brief period during which the tricot fabric is applied forming a strong bond without adhesive. It should be noted that the fabric side of the laminate is used on the outer surface of the envelope so that the hook-like members of a Velcro or Aplix fastener on the bottom of the blocks 15 and 16 hold the blocks 15 and 16 in position until the straps 22 and 23 are inserted through the rings 12, 12', 13, 13' and fastened in place.

The head blocks 14 and 15 are preferably made of e medium 2.8 pound density foam with a 100 ILD (Indentation Load Deflection) which is a product of Scott Foam of New York, N.Y. Blocks have also been made from an EVA (ethyl/vinyl acetate) foam with a two pound density, condition medium. The EVA foam is available from Monarch Rubber Co. of Baltimore, Md. In some cases it may also be desirable to coat the blocks with a hypoallergenic water-based or solvent-based vinyl dip, such as one which is available from Continental Products, Inc. of Euclid, Ohio to form a fluid impermeable coating thereon. Such blocks can then be Washed with warm soapy water and reused. In other cases, it has been found desirable to dip the blocks in a solvent hypoellergenic dip.

It should also be noted that the head blocks disclosed herein, i.e., having a unique contained shape, can be made in various sizes to fit various patient sizes, i.e. adult, young adult and children.

While the invention has been described in connection with its preferred embodiments, it should be understood that numerous changes and modifications can be made without departing from the scope of the claims.

What is claimed is:

1. A head restraint system for use in transporting an injured patient on a longitudinally extending spine/backboard comprising a stretchable base pad defining a rectangular envelope having superposed top and bottom layers which are closed along at least a portion of each of three sides thereof and open on a fourth side and constructed and arranged so that the envelope can be stretched in a lateral direction parallel to its open side and slipped over one end of the spine/backboard and pulled downwardly along the spine/backboard's longitudinal axis until one of the closed sides opposite from said open side and between said lateral sides engage the end of the spine/backboard and upon release of the lateral stretched sides tightly engages the sides of the spine/backboard, a pair of longitudinally extending head blocks having base portions adapted to engage said top layer and upwardly extending portions adapted to engage the side of a patient's head means for holding said blocks on said top layer on each side of the patient's head, fastening means fixed to said closed portion of one of said lateral sides of said envelope and strap means for engaging said fastening means and for pressing said blocks downwardly against said top layer and inwardly against the side of the patient's head to thereby prevent movement of the patient's head during movement of the patient.

2. A head restraint system according to claim 1 wherein each of said upwardly extending portions defining an opening therethrough so that a paramedic or physician can view the interior of the patient's ears without removing the blocks from the sides of the patient's head.

3. A head restraint system according to claim 2 in which said fastening means comprises a pair of ring-shaped elements.

4. A head restraint system according to claim 3 in which said fastening means includes a pair of D-shaped rings fixed to each of said lateral sides or edges of said base pad.

5. A head restraint system according to claim 4 in which said strap means includes a pair of straps each of which includes a fabric and hook-like attachment means and wherein the hook-like attachment means are fixed to each end of each of said straps.

6. A head restraint system according to claim 5 in which each of the three sides are open on a portion thereof so that the corners of the spine/backboard can extend therethrough.

7. A head restraint system according to claim 2 in which each of said pair of blocks includes means for inflating said blocks and means for closing or sealing the inflation means.

8. A head restraint system according to claim 2 in which each of said upwardly extending portions of said longitudinally extending contoured head blocks defines converging concave and convex surfaces which curve upwardly from said base portion and come together at the top of said upwardly extending portion and wherein concave surface is adapted to engage the head of a patient.

9. A head restraint system according to claim 8 in which each of said longitudinally extending blocks comprises a foam core and a relatively flexible fluid impervious hypoallergenic coating thereon.

* * * * *